United States Patent [19]

Becher et al.

[11] Patent Number: 4,792,626

[45] Date of Patent: Dec. 20, 1988

[54] PRODUCTION OF AROMATIC DIAMINO COMPOUNDS USING A MODIFIED RANEY CATALYST

[75] Inventors: Dieter Becher, Dormagen; Udo Birkenstock, Ratingen; Eckart Waldau, Düsseldorf; Harro Witt, Kuden, all of Fed. Rep. of Germany

[73] Assignee: Bayer Aktiengesellschaft, Bayerwerk, Fed. Rep. of Germany

[21] Appl. No.: 917,449

[22] Filed: Oct. 10, 1986

[30] Foreign Application Priority Data

Oct. 19, 1985 [DE] Fed. Rep. of Germany ....... 3537247

[51] Int. Cl.$^4$ ............................................. C07C 85/11
[52] U.S. Cl. ..................................... 564/422; 564/421
[58] Field of Search ................................. 564/422, 421

[56] References Cited

U.S. PATENT DOCUMENTS

| | | | |
|---|---|---|---|
| 3,544,485 | 12/1970 | Taira et al. | 564/422 X |
| 3,761,521 | 9/1973 | Alheritiere et al. | 260/580 |
| 3,895,065 | 7/1975 | Alheritiere et al. | 260/583 |
| 4,287,365 | 9/1981 | Becker et al. | 564/422 |

FOREIGN PATENT DOCUMENTS

| | | | |
|---|---|---|---|
| 0091027 | 10/1983 | European Pat. Off. | 564/422 |
| 1066582 | 2/1953 | France | 564/422 |
| 1044099 | 6/1957 | Fed. Rep. of Germany | 564/422 |
| 3315191 | 10/1984 | Fed. Rep. of Germany | 564/422 |
| 084508 | 12/1977 | Japan | 564/422 |
| 035064 | 5/1978 | Japan | 564/422 |
| 919273 | 2/1963 | United Kingdom | 564/422 |

*Primary Examiner*—Paul F. Shaver
*Attorney, Agent, or Firm*—Gene Harsh; Joseph C. Gil; Lyndanne M. Whalen

[57] ABSTRACT

Aromatic diamino compounds are produced by hydrogenating the corresponding dinitro compounds in the presence of a modified Raney catalyst. The modified Raney catalyst is obtained by treating an alloy made up of 50-95 wt % of aluminum, 4-45 wt % nickel and/or cobalt and 1-46 wt % of at least one modifying metal with an alkali material. The modifying metal is selected from the metals of the first, fourth, fifth, sixth, seventh and eighth subgroups of the Periodic Table of Elements. The hydrogenation is preferably carried out at from 170° to 250° C. and a pressure of 15-50 bar. The heat generated during hydrogenation is preferably used to produce steam.

4 Claims, No Drawings

PRODUCTION OF AROMATIC DIAMINO COMPOUNDS USING A MODIFIED RANEY CATALYST

BACKGROUND OF THE INVENTION

This invention relates to the production of aromatic diamino compounds by hydrogenating aromatic dinitro compounds in the presence of a modified Raney catalyst.

The catalytic hydrogenation of aromatic dinitro coapounds, such as dinitrotoluene, using suspended Raney catalysts is known (see, e.g. DE-AS No. 1,044,099 and FR-PS No. 1,599,004). Such hydrogenation generally takes place at temperatures below 170° C., preferably at temperatures of from 50° to 150° C. The heat of the hydrogenation reaction is deliberately lost in order to obtain the desired diamines in high yields and at high purities.

Processes which allow a reaction to be carried out at high temperatures, such as that described in DE-OS No. 3,315,191, require improved catalysts having increased selectivity and elevated temperature resistance. Important secondary reactions in this context are hydrogenation and deamination of the aromatic moieties, as well as the formation of high molecular weight compounds.

SUMMARY OF THE INVENTION

It has been found that use of modified Raney catalysts in the hydrogenation of aromatic dinitro compounds to form aromatic diamino compounds makes it possible to employ reaction conditions which allow the heat of the hydrogenation reaction to be recovered in a technically useful form (for example, as steam) without sacrificing product quality and yields. The higher the reaction temperature which may be selected without yield losses, the greater the economic value. The steam obtained from the heat of the reaction may be used in the course of working-up the diamine or it may be supplied to other energy consumers.

It has also been found that the limitations of the prior art processes when carried out on a large scale may be overcome by using the modified Raney catalysts required in the claimed invention.

DETAILED DESCRIPTION OF THE INVENTION

The present invention relates to a process for the production of aromatic diamino compounds by hydrogenating the corresponding aromatic dinitro compound in the presence of a modified Raney catalyst. The Raney catalyst is a product of an alkali treatment of an alloy of from 50 to 95 wt % (preferably from 60 to 85 wt %) of aluminum, from 4 to 45 wt % (preferably from 10 to 30 wt %) of nickel and/or cobalt and from 1 to 46 wt % (preferably from 5 to 15 wt %) of at least one modifying metal, the percentages totalling 100. The modifying metal is selected from the metals of the 1st, 4th, 5th, 6th, 7th and/or 8th subgroups of the Periodic Table of the Elements.

In the present invention, Raney catalysts modified with iron, ruthenium, rhenium, chromium, molybdenum, tungsten, niobium, tantalum, vanadium, titanium, copper, zirconium and/or hafnium are preferred.

The alkali treatment of the Raney catalyst may be carried out by reacting the alloy with an aqueous solution of an alkali metal hydroxide (for example, sodium or potassium hydroxide) or, less preferably, an alkali metal carbonate (e.g., sodium or potassium carbonate). This reaction is preferably carried out at an elevated temperature (e.g., from about 50° to 100° C.). The catalyst is then filtered off and freed from the majority of the alkaline constituents by washing with water (for example, distilled, de-ionized and/or drinking water). The amount of base is dependent on the quantity of aluminum present in the alloy. The bases may be used in an amount which, with respect to the conversion of the total quantity of aluminum to alkali metal aluminate, is sub-stoichiometric or stoichiometric. The alkali compounds are preferably used, however, in a stoichiometric excess with respect to aluminate formation.

The treated catalysts may also contain residual quantities of aluminum. This residual quantity of aluminum is generally from 1 to 70 wt %, preferably from 1 to 10 wt %. The weight ratio of nickel and/or cobalt to the modifying metals in the catalyst is generally from 30:70 to 99:1, preferably from 50:50 to 90:10.

The catalysts employed in the present invention are modified skeleton catalysts of the Raney type and are generally in the form of moist powders having an average particle size of $<130$ μm, preferably $<80$ μm. Average particle size may be determined by a laser granulometer in known manner.

Catalysts similar to those employed in the present invention are described in Japanese Patent Applications No. 54 084-508 of 15.12.77, published on 5.7.79 under the number 152 098 and 55 035 - 064 of 5.9.78, published on 11.3.80 under the number 109 240. These disclosed catalysts are taught to be useful for the reduction of aldehydes. The good stability of such catalysts in the hydrogenation of aromatic dinitro compounds (a completely different reaction carried out under varying reaction conditions) and the possibility of using the reaction heat (not a concern in aldehyde reduction processes) is neither obvious nor predictable from these Japanese disclosures.

Starting materials useful in the present invention are any aromatic dinitro compounds. Specific examples include: 1,3-dinitrobenzene, 1,5-dinitronaphthalene, 1,8-dinitronaphthalene and isomers of dinitrotoluene and mixtures thereof. The catalysts used in the present invention are particularly suitable for the catalytic hydrogenation of 2,4-dinitrotoluene and technical mixtures thereof with up to 40 wt % (based on the total mixture) of 2,6-dinitrotoluene.

The dinitro compounds are preferably hydrogenated without a solvent, at a temperature of from 170° to 250° C. and under a pressure of from 15 to 50 bar (in the absence of solvent) or from 15 to 120 bar (in the presence of solvent) in the presence of the modified Raney catalysts dispersed in the reaction medium. Dinitro compounds which are solid at room temperature are generally melted before hydrogenation is carried out.

The hydrogenation may take place either discontinuously or continuously using conventional reactors. The hydrogenation may be carried out, for example, continuously in a reactor of the type described in Example 2, which has been filled with a suspension of the catalyst in the process product (mixture of diamine and water) before charging with the dinitro compound to be hydrogenated. During the continuous process in such a reactor, the quantity of the dinitro compound fed into the reactor usually corresponds to the quantity of process product simultaneously removed. The average residence time of the reaction mixture in the reactor is dependent upon the throughput of the aromatic dinitro compound, the type and quantity of the catalyst used and the reactor volume but is generally from 1 minute to 3 hours.

It is one of the advantages of the present invention that the hydrogenation reactions may be carried out without the simultaneous use of an inert solvent. The simultaneous use of such solvents, for example, aliphatic alcohols having up to 6 carbon atoms, such as methanol, isopropanol and t-butanol; ketones having up to 9 carbon atoms such as acetone and/or methylisobutyl ketone: and/or carboxylic acids such as acetic acid, is not excluded, but is less preferred.

The heat of reaction due to the comparatively high reaction temperature, may be used for the production of steam in known manner with output pressures of from 5 to 30 bar.

The invention is further illustrated, but is not intended to be limited by the following examples in which all parts and percentages are by weight unless otherwise specified.

EXAMPLES

Example 1 (Production of a catalyst)

782 g of sodium hydroxide were dissolved in a beaker in 3129 g of water. The temperature of the sodium hydroxide solution was adjusted to 80° C. The air over the solution was exchanged for nitrogen, so that the process could be carried out under a nitrogen atmosphere over the total reaction time.

A total of 200 g of an alloy of 80 parts of aluminum, 14 parts of nickel and 6 parts of iron were then added to the sodium hydroxide solution in portions of 6 g in each case. A strongly exothermic reaction with substantial foam formation occurred in each case. The addition of the alloy took place over a period of 20 min. in a manner such that the temperature of the sodium hydroxide was maintained at 80° C.±2° C. and the foam formation did not increase too substantially.

When the total quantity of alloy had been added, the reaction mixture was stirred for 30 min. at 80° C. The mother liquor was then decanted off from the catalyst and the catalyst was subsequently treated with stirring with a washing liquor made up of 78 g of sodium hydroxide and 313 g of water for 5 min. The washing liquor was then separated by decantation and the catalyst was washed with water to a pH of about 8.0. 105 g of catalyst slurry were obtained. The weight ratio of nickel to iron was 69:31.

Example 2

An autoclave having a liquid volume of 80 ml, provided with a gassing stirrer, a hydrogen supply conduit, an inlet tube for the aromatic dinitro compound the lower end of which ended directly at the gassing stirrer, and an outlet valve for excess hydrogen was used. The reaction mixture made up of an aromatic diamine and water left the reactor through a frit which retained the catalyst. The apparatus made possible the continuous hydrogenation of the aromatic dinitro compound until the catalyst was completely exhausted. The temperature in the reactor was controlled by exterior heating or cooling circulation (a cooling coil in the interior of the reactor could provide for additional cooling of the reaction mixture).

80 ml of a mixture of (i) a mixture of 80% of 2,4-diaminotoluene and 20% of 2,6-diaminotoluene with (ii) water in the weight ratio (i):(ii) 63:37, in which 1.6 g of the catalyst according to Example 1 were present in a suspended state were placed in the reactor. The reactor contents were then heated to 175° C. under a hydrogen atmosphere at a pressure of 20 bar. At this temperature, 64 l of hydrogen and 53 g of DNT (mixture of 80% of 2,4-dinitrotoluene and 20% of 2,6-dinitrotoluene) were conducted into the reactor every hour by means of a metering pump. The temperature in the reactor rose to 190° C. At this temperature and under a pressure of 20 bar, hydrogenation took place until the catalyst was exhausted (50 h). The resulting process product (mixture of diamine and water) was continuously removed, and pure diaminotoluene isomer mixture (TDA) was recovered therefrom by distilation. The yield of pure TDA (80:20) corresponded to 98.7% of the theoretical value, based on the DNT used. During working-up by distillation, 1.1% of tarry by-products and 0.2% of "low-boiling products" were obtained.

Example 3

A modified Raney-nickel produced by alkali treatment of an alloy of 80% of aluminum, 10% of nickel and 10% of molybdenum in accordance with the procedure used in Example 1 was used as the catalyst. The weight ratio of nickel:molybdenum in the catalyst was 74:26.

The process was carried out in the apparatus described in Example 2 at a temperature of 220° C. and under a pressure of 30 bar and 53 g/h of DNT in the same manner described in Example 2. The contents of the reactor before commencement of reaction (diamine and water) contained 0.8 g of catalyst in a suspended state. The yield of TDA corresponded to 99.2% of the theoretical value, based on the DNT used. In addition, 0.75% of tarry products and 0,05% by-products boiling lower than TDA ("low-boiling products") formed.

Examples 4 to 14

Example 2 was repeated using the catalysts, temperatures and pressures set out in the following Table. The catalysts were each produced in a manner analogous to that used to produce the catalyst of Example 1 using the aliquot quantity of sodium hydroxide solution, based on the aluminum content of the alloy. The figures given in the formulae following the elements relate to the percentage composition of the alloys or to the weight ratios of the nickel or modifying metal present in the catalysts. The catalysts also contained a fluctuating residual quantity of aluminum (1 to 10%). In Example 13, the process was carried out with the simultaneous use of isopropanol as solvent. This is a 30 wt % solution of TDA/water (63:37) in which the catalyst present in a suspended state was used for filling the reactor before commencement of reaction and the DNT to be hydrogenated was used as a 33 wt % solution in isopropanol. The total quantity of solution continuously fed in corresponded to the use of 126 g/h of DNT. The results of Examples 4 to 14 are set out in the following Table.

TABLE

| Example | Alloy | Catalyst | t (°C.) | p (bar) | TDA-yield (%) |
|---|---|---|---|---|---|
| 4 | Al(80)Ni(15)Nb(5) | RaNi(81)Nb(19) | 220 | 30 | 97.5 |
| 5 | Al(85)Ni(14)Ra(1) | RaNi(94)Ta(6) | 220 | 30 | 98 |

TABLE-continued

| Example | Alloy | Catalyst | t (°C.) | p (bar) | TDA-yield (%) |
|---|---|---|---|---|---|
| 6 | Al(80)Ni(14)W(6) | RaNi(93)W(7) | 220 | 30 | 97 |
| 7 | Al(70)Ni(25.5)Ti(4.5) | RaNi(86)Ti(14) | 190 | 30 | 98.2 |
| 8 | Al(70)Ni(25.5)V(4.5) | RaNi(98)V(2) | 190 | 30 | 98.7 |
| 9 | Al(80)Ni(14)Cr(6) | RaNi(77)Cr(23) | 190 | 30 | 97.5 |
| 10 | Al(80)Ni(14)Cu(6) | RaNi(70)Cu(30) | 220 | 30 | 98.9 |
| 11 | Al(80)Ni(14)Mo(6) | RaNi(88)Mo(12) | 220 | 30 | 99 |
| 12 | Al(80)Ni(12)Fe(6)Mo(2) | RaNi(64)Fe(32)Mo(4) | 190 | 30 | 99 |
| 13 | Al(80)Ni(14)Fe(6) | RaNi(69)Fe(31) | 220 | 80 | 98 in isopropanol |
| 14 | Al(90)Ni(7)Fe(3) | RaNi(75)Fe(25) | 190 | 30 | 98.7 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of aromatic diamines in which an aromatic dinitro comound is hydrogenated in the presence of a modified Raney catalyst which modfied Raney catalyst is the product of an alloy treated with an alkali material which alloy is made up of
   (a) 50-95 wt % aluminum,
   (b) 4-45 wt % nickel and/or cobalt and
   (c) 1-46 wt % of at least one modifying metal selected from the first, fourth, fifth, sixth, seventh and eighth subgroups of the Periodic Table of Elements
   with the percentages totalling 100 wt % in which the hydrogenation is carried out at a temperature of from 170° to 250° C. and pressure of from 15 to 50 bar in the absence of an auxiliary solvent.

2. The process of claim 1 in which the modifying metal is selected from iron, chromium, copper, molybdenum, tantalum, tungsten, vanadium, titanium, niobium, rhenium, ruthenium, zirconium and hafnium.

3. The process of claim 1 in which the heat generated during the hydrogenation is used to produce steam at pressures of from 5 to 30 bar.

4. The process of claim 2 in which the modifying metal (c) is selected from chromium, copper, molybdenum, tantalum, tungsten, vanadium, titanium, niobium, rhenium, ruthenium, zirconium and hafnium.

* * * * *